US00PP35019P2

(12) United States Plant Patent
Wood

(10) Patent No.: US PP35,019 P2
(45) Date of Patent: Mar. 7, 2023

(54) ILEX PLANT NAMED 'SMNIGLA'

(50) Latin Name: *Ilex glabra*
Varietal Denomination: SMNIGLA

(71) Applicant: Timothy D. Wood, Spring Lake, MI (US)

(72) Inventor: Timothy D. Wood, Spring Lake, MI (US)

(73) Assignee: SPRING MEADOW NURSERY INC., Grand Haven, MI (US)

( * ) Notice: Subject to any disclaimer, the term of this patent is extended or adjusted under 35 U.S.C. 154(b) by 0 days.

(21) Appl. No.: 17/953,191

(22) Filed: Sep. 26, 2022

(51) Int. Cl.
*A01H 6/00* (2018.01)
*A01H 5/02* (2018.01)

(52) U.S. Cl.
USPC ..... Plt./247

(58) Field of Classification Search
USPC ..... Plt./247
CPC ..... A01H 6/00; A01H 5/02
See application file for complete search history.

*Primary Examiner* — Keith O. Robinson
(74) *Attorney, Agent, or Firm* — C. Anne Whealy

(57) ABSTRACT

A new and distinct *Ilex* plant named 'SMNIGLA', characterized by its compact and upright conical plant habit; freely branching habit; dense and bushy growth habit; dark green-colored leaves that are slightly curled or undulate; and good garden performance.

2 Drawing Sheets

Figure 1:
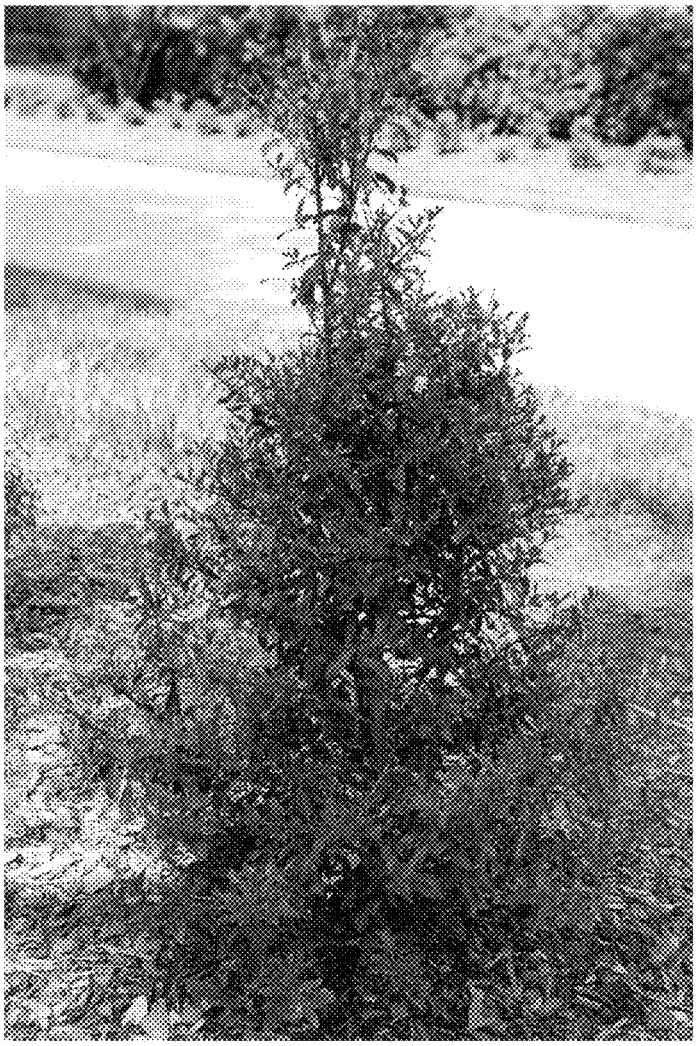

Botanical designation: *Ilex glabra.*
Cultivar denomination: 'SMNIGLA'.

BACKGROUND OF THE INVENTION

The present Invention relates to a new and distinct *Ilex* plant, botanically known as *Ilex glabra*, commonly referred to as Inkberry or Gallberry and hereinafter referred to by the name 'SMNIGLA'.

The new *Ilex* plant is a product of a planned breeding program conducted by the Inventor in Grand Haven, Mich. The objective of the breeding program was to develop new uniform *Ilex* plants that are unique in plant form.

The new *Ilex* plant originated from an open-pollination in 2008 of an unnamed proprietary selection of *Ilex glabra*, not patented, as the female, or seed, parent with an unknown selection of *Ilex glabra*, as the male, or pollen, parent. The new *Ilex* plant was discovered and selected by the Inventor in 2010 as a single plant within the progeny of the stated open-pollination in a controlled environment in Grand Haven, Mich.

Asexual reproduction of the new *Ilex* plant by softwood cuttings in Grand Haven, Mich. since 2010 has shown that the unique features of the new *Ilex* plant are stable and reproduced true to type in successive generations of asexual reproduction.

SUMMARY OF THE INVENTION

Plants of the new *Ilex* have not been observed under all possible combinations of environmental conditions and cultural practices. The phenotype may vary somewhat with variations in environmental conditions such as temperature and light intensity without, however, any variance in genotype. The following traits have been repeatedly observed and are determined to be the unique characteristics of 'SMNIGLA'. These characteristics in combination distinguish 'SMNIGLA' as a new and distinct *Ilex* plant:

1. Compact and upright conical plant habit.
2. Freely branching habit; dense and bushy growth habit.

3. Dark green-colored leaves that are slightly curled or undulate.
4. Good garden performance.

Plants of the new *Ilex* differ primarily from plants of the female parent selection in plant habit as plants of the new *Ilex* are upright conical whereas plants of the female parent selection are upright rounded. In addition, plants of the new *Ilex* only produce male flowers and are not fruit-producing whereas plants of the female parent selection produce female flowers and are fruit-producing.

Plants of the new *Ilex* can be compared to the plants of *Ilex glabra* 'SMNIGAB17', disclosed in U.S. Plant Pat. No. 27,554. In side-by-side comparisons, plants of the new *Ilex* differ from plants of 'SMNIGAB17' in the following characteristics:

1. Plants of the new *Ilex* are upright conical in plant habit whereas plants of 'SMNIGAB17' are low-mounding and globose in plant habit.
2. Plants of the new *Ilex* only produce male flowers and are not fruit-producing whereas plants of 'SMNIGAB17' produce female flowers and are fruit-producing.

BRIEF DESCRIPTION OF THE PHOTOGRAPHS

The accompanying colored photographs illustrate the overall appearance of the new *Ilex* plant. The photographs show the colors as true as it is reasonably possible to obtain in colored reproductions of this type. Colors in the photographs may differ slightly from the color values cited in the detailed botanical description which accurately describe the colors of the new *Ilex* plant.

The photograph on the first sheet (FIG. 1) is a side perspective view of a typical plant of 'SMNIGLA' grown in an outdoor nursery.

Figure 2:
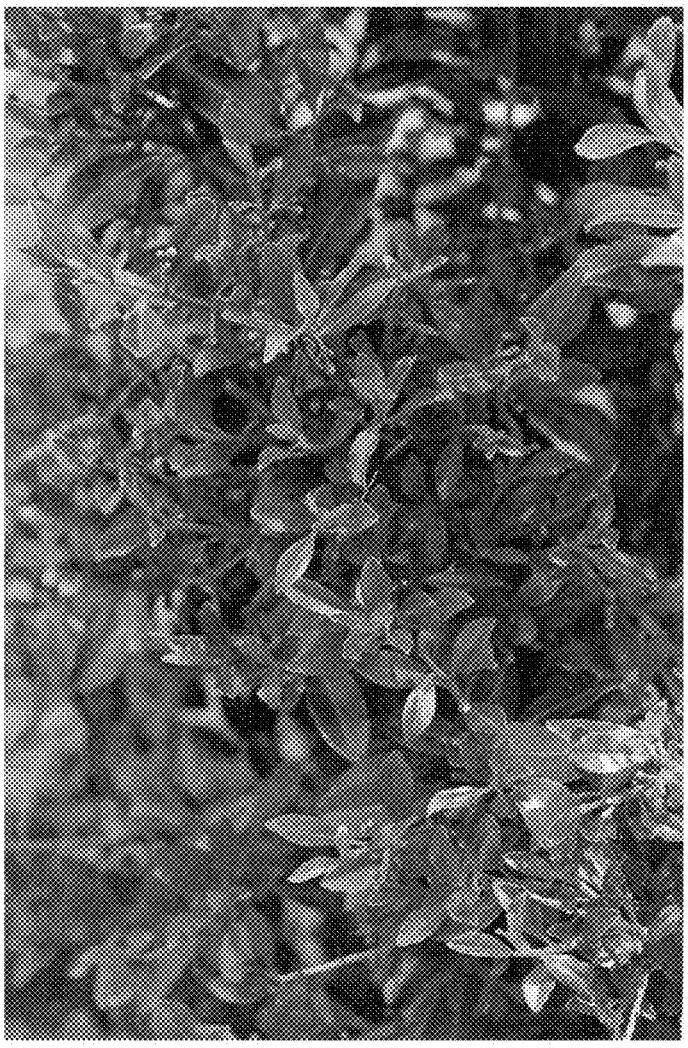

The photograph on the second sheet (FIG. 2) is a close-up view of a typical plants of 'SMNIGLA'.

DETAILED BOTANICAL DESCRIPTION

The aforementioned photographs and following observations and measurements describe plants grown during the spring and early summer in three-gallon containers in a polyethylene-covered greenhouse and outdoor nursery in Grand Haven, Mich. and under cultural practices typical of commercial *Ilex* production. During the production of the plants, day temperatures ranged from 18° C. to 27° C. and night temperatures ranged from ranged from 5° C. to 10° C. Plants were three years old when the photographs and detailed description were taken. In the following description, color references are made to The Royal Horticultural Society Colour Chart, 2015 Edition, except where general terms of ordinary dictionary significance are used.

Botanical classification: *Ilex glabra* 'SMNIGLA'.

Parentage:

*Female, or seed, parent.*—Unnamed proprietary selection of *Ilex glabra*, not patented.

*Male, or pollen, parent.*—Unknown selection of *Ilex glabra*, not patented.

Propagation:

*Type.*—By softwood cuttings.

*Time to initiate roots, winter.*—About eight to ten weeks at temperatures about 4.4° C.

*Time to produce a rooted young plant, winter.*—About three to four months at temperatures about 4.4° C.

*Root description.*—Fine, fibrous; typically grey brown and creamy white in color, actual color of the roots is dependent on substrate composition, water quality, fertilizer, substrate temperature and physiological age of roots.

*Rooting habit.*—Freely branching; medium density to dense.

Plant description:

*Plant and growth habit.*—Perennial evergreen shrub; compact and upright conical plant habit; vigorous growth habit and moderate growth rate.

*Branching habit.*—Freely branching habit; dense and bushy growth habit with about 30 to 40 lateral branches developing per plant.

*Plant height.*—About 60 cm.

*Plant diameter, area of spread.*—About 30 cm.

*Lateral branch description.*—Length: About 15 cm. Diameter: About 2 mm to 3 mm. Internode length: About 5 mm. Strength: Strong. Aspect: About 45° to 90° from vertical. Texture: Smooth, glabrous; becoming woody with development. Color, developing: Close to 145A. Color, developed: Close to 197B to 197C.

*Leaf description.*—Arrangement: Alternate, simple. Length: About 2.5 cm. Width: About 1 cm. Shape: Narrowly elliptic to oblong; slightly curled and undulate. Apex: Acute. Base: Attenuate. Margin: Proximally, entire and distally, serrulate. Venation pattern: Pinnate. Texture and luster, upper surface: Smooth, glabrous; glossy. Texture and luster, lower surface: Smooth, glabrous with prominent midvein; somewhat glossy. Color: Developing leaves, upper and lower surfaces: Close to 146A. Fully expanded leaves, upper surface: Close to 147A; venation, close to 146B. Fully expanded leaves, lower surface: Close to 146B; venation, close to 146B. Petioles: Length: About 5 mm. Diameter: About 1 mm. Texture, upper and lower surfaces: Smooth, glabrous. Color, upper and lower surfaces: Close to 146B.

Flower description:

*Flower appearance and arrangement.*—Single terminal and axillary rotate flowers arranged in clusters of three to four flowers; about 40 flower buds and flower buds per lateral branch; flowers staminate; flowers face mostly outwardly.

*Natural flowering season.*—Plants flower in April in Michigan; flowers not persistent.

*Fragrance.*—None detected.

*Flower diameter.*—About 8 mm.

*Flower depth.*—About 2 mm.

*Flower buds.*—Length: About 3 mm. Diameter: About 2 mm. Shape: Orbicular. Color: Close to 145B.

*Petals.*—Quantity and arrangement: About five in a single whorl; fused at the base. Length: About 4 mm. Width: About 4 mm. Shape: Orbicular to broadly elliptic. Apex: Obtuse. Margin: Entire. Texture, upper and lower surfaces: Smooth, glabrous; soft. Color: When opening, upper and lower surfaces: Close to NN155B. Fully opened, upper and lower surfaces: Close to NN155B; color does not change with subsequent development.

*Sepals.*—Quantity and arrangement: About five in a single whorl; fused at the base. Length: Less than 1 mm. Diameter: Less than 1 mm. Shape: Obovate. Apex: Acute. Margin: Entire. Texture, upper and lower surfaces: Smooth, glabrous. Color, upper and lower surfaces: Close to 145B.

*Peduncles.*—Length: About 3 mm. Diameter: About 1 mm. Aspect: About 45° from lateral branch axis. Strength: Strong; slightly flexible. Texture: Smooth, glabrous. Color: Close to 145B.

*Reproductive organs.*—Androecium: Quantity per flower: About five. Filament length: About 3 mm. Filament color: Close to NN155B. Anther length: About 1 mm. Anther shape: Oblong. Anther color: Close to 1C. Pollen amount: Scarce. Pollen color: Close to 1D.

Garden performance: Plants of the new *Ilex* have been observed to have good garden performance.

Pathogen & pest resistance: To date, plants have not been observed to be resistant to pathogens and pests common to *Ilex* plants.

It is claimed:

1. A new and distinct *Ilex* plant named 'SMNIGLA' as illustrated and described.

* * * * *